US012759963B2

(12) United States Patent
Ni et al.

(10) Patent No.: US 12,759,963 B2
(45) **Date of Patent: *Oct. 13, 2026**

(54) METHOD FOR PREPARING GLYCOLIC ACID THROUGH HYDROLYSIS OF ALKOXYACETATE

(71) Applicant: DALIAN INSTITUTE OF CHEMICAL PHYSICS, CHINESE ACADEMY OF SCIENCES, Dalian (CN)

(72) Inventors: Youming Ni, Dalian (CN); Wenliang Zhu, Dalian (CN); Zhongmin Liu, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 559 days.

This patent is subject to a terminal disclaimer.

(21) Appl. No.: 18/275,447

(22) PCT Filed: Feb. 3, 2021

(86) PCT No.: PCT/CN2021/075027

§ 371 (c)(1),
(2) Date: Aug. 2, 2023

(87) PCT Pub. No.: WO2022/165663

PCT Pub. Date: Aug. 11, 2022

(65) Prior Publication Data

US 2024/0116844 A1 Apr. 11, 2024

(51) Int. Cl.
*C07C 59/06* (2006.01)
*B01J 29/40* (2006.01)
*B01J 29/70* (2006.01)
*C07C 51/09* (2006.01)

(52) U.S. Cl.
CPC ............... *C07C 59/06* (2013.01); *B01J 29/40* (2013.01); *B01J 29/7038* (2013.01); *C07C 51/09* (2013.01); *C07C 2529/40* (2013.01)

(58) Field of Classification Search
CPC ..... C07C 51/09; C07C 59/06; C07C 2529/40; B01J 29/40; B01J 29/7038
See application file for complete search history.

(56) References Cited

U.S. PATENT DOCUMENTS

2018/0201557 A1 7/2018 Ni et al.

FOREIGN PATENT DOCUMENTS

| | | | | |
|---|---|---|---|---|
| CN | 1180067 A | * | 4/1998 | ............. C07C 67/31 |
| CN | 101538187 A | | 9/2009 | |
| CN | 102531883 A | | 7/2012 | |
| CN | 104119228 A | | 10/2014 | |
| CN | 106365999 A | | 2/2017 | |
| CN | 106554250 A | | 4/2017 | |
| CN | 108689844 A | | 10/2018 | |
| CN | 107445825 B | | 10/2019 | |
| JP | 2003300926 A | | 10/2003 | |

OTHER PUBLICATIONS

Fuat E. Celik, et al., Vapor-Phase Carbonylation of Dimethoxymethane over H-Faujasite, Angew. Chem. Int. Ed., 2009, pp. 4813-4815, vol. 48.

August Folsing, On the Influence of Hydrogen Bromide on the Aetheresters of Oxyacids, German Chemical Society, 1884, pp. 484-486.

Ying Sun, et al., Highly effective synthesis of methyl glycolate with heteropolyacids as catalysts, Catalysis Communications, 2009, pp. 678-681, vol. 10.

Yang Tianyu, Research on the condensation of formaldehyde and methyl formate to produce methyl glycolate and methyl oxyacetic acid ester, Kunming University of Science and Technology, 2004, pp. 4-6.

Sun Fengxia, et al., Study on Preparation of Glycolic Acid by Hydrolysis of Methyl Glycolate, Industrial Catalysis, 2018, pp. 56-59, vol. 26, No. 4.

Zhou Weiyou, et al., Preparation of glyoxylic acid from methyl glycolate, Chemical Industry and Engineering Progress, 2011, pp. 2536-2539, vol. 30, No. 11.

* cited by examiner

*Primary Examiner* — Yate' K Cutliff
(74) *Attorney, Agent, or Firm* — Bayramoglu Law Offices LLC

(57) ABSTRACT

A method for preparing glycolic acid through hydrolysis of alkoxyacetate is provided. The method includes: subjecting raw materials including the alkoxyacetate and water to a reaction in the presence of an acidic molecular sieve catalyst to produce the glycolic acid, where the alkoxyacetate is at least one selected from the group consisting of compounds with a structural formula shown in formula I; and in formula I, $R_1$ and $R_2$ each are independently any one selected from the group consisting of $C_1$-$C_5$ alkyl groups. The glycolic acid production method in the present application can be implemented by a traditional fixed-bed reactor under an atmospheric pressure, which is very suitable for continuous production.

12 Claims, No Drawings

METHOD FOR PREPARING GLYCOLIC ACID THROUGH HYDROLYSIS OF ALKOXYACETATE

CROSS REFERENCE TO THE RELATED APPLICATIONS

This application is the national phase entry of International Application No. PCT/CN2021/075027, filed on Feb. 3, 2021, the entire contents of which are incorporated herein by reference.

TECHNICAL FIELD

The present application relates to a method for preparing glycolic acid through hydrolysis of alkoxyacetate, and belongs to the field of preparation of chemical products.

BACKGROUND

Glycolic acid, also known as hydroxyacetic acid, is the simplest α-hydroxycarboxylic acid compound. Because the molecular structure of glycolic acid includes both hydroxyl and carboxyl, glycolic acid can undergo self-polymerization to produce polyglycolic acid (PGA). PGA has not only excellent biocompatibility, but also safe biodegradability. Therefore, PGA is widely used not only for medical surgical sutures, drug sustained-release materials, and degradable human tissue scaffolds, but also in production of common plastic products. Conventional non-degradable plastic products have caused heavy environmental pollution, and biodegradable PGA plastics are expected to solve this problem. Glycolic acid can also undergo copolymerization with monomers such as lactic acid and hydroxypropionic acid to produce a polymer material with excellent performance and extensive applications. In addition, glycolic acid is an excellent chemical cleaning agent and cosmetic raw material.

Preparation methods of glycolic acid mainly include a chloroacetic acid hydrolysis method, a formaldehyde carbonylation method, and an oxalate hydrogenation/hydrolysis method. In the chloroacetic acid hydrolysis method, the preparation process of the raw material chloroacetic acid causes heavy pollution, and the hydrolysis process of chloroacetic acid leads to a large amount of waste salt, heavy pollution, and poor quality product. Thus, the chloroacetic acid hydrolysis method has been basically eliminated. The formaldehyde carbonylation method involves cheap and easily-available raw materials, but needs to be implemented under conditions such as a high temperature, a high pressure, a strong liquid acid, and an organic solvent. In addition, in the formaldehyde carbonylation method, the device is easily corroded, and the product purification is difficult, resulting in a high industrial production cost. In the oxalate hydrogenation/hydrolysis method, an oxalate is partially hydrogenated to produce methyl glycolate, and then methyl glycolate is hydrolyzed to produce glycolic acid. However, the catalyst for partial hydrogenation of the oxalate is not mature and has low conversion efficiency and poor stability; and the oxalate production process is cumbersome and costly. These problems seriously restrict the development of the oxalate hydrogenation/hydrolysis method.

SUMMARY

According to the problems faced by the existing production technologies of glycolic acid ($HOCH_2COOH$), the present disclosure discloses a method for preparing glycolic acid through hydrolysis of alkoxyacetate. The method of the present application is particularly suitable for carbonylation of DMM produced in the coal chemical industry to produce methyl methoxyacetate and then hydrolysis to produce glycolic acid.

A method for preparing glycolic acid through hydrolysis of alkoxyacetate is provided, including: subjecting raw materials including the alkoxyacetate and water to a reaction in the presence of an acidic molecular sieve catalyst to produce the glycolic acid, where the alkoxyacetate is at least one selected from the group consisting of compounds with a structural formula shown in formula I:

formula I

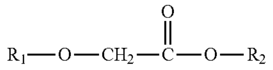

where $R_1$ and $R_2$ each are independently any one selected from the group consisting of $C_1$-$C_6$ alkyl groups.

The present application discloses a method for preparing glycolic acid through hydrolysis of alkoxyacetate, where raw materials of alkoxyacetate and water are allowed to pass through a reaction zone loaded with an acidic molecular sieve catalyst, such that the raw materials undergo a reaction under specified conditions to produce glycolic acid. The hydrolysis catalyst used in the present application is a molecular sieve catalyst with long life and high hydrolysis efficiency. The glycolic acid production method in the present application can be implemented by a traditional fixed-bed reactor under an atmospheric pressure, which is very suitable for continuous production. The raw material alkoxyacetate in the present application can be prepared by an environmentally-friendly and economical acetal carbonylation method. When the raw material in the present application is methyl methoxyacetate, methanol and formaldehyde condensation to prepare dimethoxymethane (DMM), DMM carbonylation to prepare methyl methoxyacetate, and methyl methoxyacetate hydrolysis to prepare glycolic acid can be used in combination to allow efficient, environmentally-friendly, and economical conversion of methanol (a platform chemical in the coal chemical industry) into glycolic acid.

Preferably, $R_1$ is any one selected from the group consisting of methyl, ethyl, propyl, and butyl; and $R_2$ is any one selected from the group consisting of methyl, ethyl, propyl, and butyl.

Specifically, the alkoxyacetate is any one selected from the group consisting of methyl methoxyacetate, ethyl methoxyacetate, n-propyl methoxyacetate, n-butyl methoxyacetate, and ethyl ethoxyacetate.

Further preferably, the alkoxyacetate is methyl methoxyacetate.

In recent years, the DMM carbonylation reaction to prepare methyl methoxyacetate has received widespread attention. This reaction is based on a molecular sieve catalyst, can be conducted at a low reaction temperature, and has high atomic economy. The raw material DMM can be produced by a very mature industrialized technology with high efficiency, and thus is cheap. In the present application, the hydrolysis of ether and ester bonds of methyl methoxyacetate to prepare glycolic acid becomes an environmentally-friendly and economical production path for glycolic acid.

Optionally, the acidic molecular sieve catalyst includes an acidic molecular sieve.

Optionally, the acidic molecular sieve is at least one selected from the group consisting of an acidic MFI-structured molecular sieve, an acidic FAU-structured molecular sieve, an acidic FER-structured molecular sieve, an acidic BEA-structured molecular sieve, an acidic mordenite (MOR)-structured molecular sieve, and an acidic MWW-structured molecular sieve.

Preferably, the acidic molecular sieve is any one selected from the group consisting of an acidic MFI-structured molecular sieve and an acidic FER-structured molecular sieve.

Optionally, the acidic molecular sieve is at least one selected from the group consisting of an acidic ZSM-5 molecular sieve, an acidic Y molecular sieve, an acidic ZSM-35 molecular sieve, an acidic β molecular sieve, an acidic MOR molecular sieve, and an acidic MCM-22 molecular sieve.

Preferably, the acidic molecular sieve is at least one selected from the group consisting of a hydrogen-type ZSM-5 molecular sieve, a hydrogen-type Y molecular sieve, a hydrogen-type ZSM-35 molecular sieve, a hydrogen-type β molecular sieve, a hydrogen-type MOR molecular sieve, and a hydrogen-type MCM-22 molecular sieve.

Further preferably, the acidic molecular sieve is any one selected from the group consisting of a hydrogen-type ZSM-5 molecular sieve and a hydrogen-type ZSM-35 molecular sieve.

Optionally, a Si/Al atom ratio of the acidic molecular sieve is 3 to 500.

Specifically, an upper limit of the Si/Al atom ratio of the acidic molecular sieve is selected from the group consisting of 10, 20, 50, 100, and 500; and a lower limit of the Si/Al atom ratio of the acidic molecular sieve is selected from the group consisting of 3, 10, 20, 50, and 100.

Optionally, the acidic molecular sieve catalyst further includes a forming agent; and the forming agent is an oxide.

Optionally, the oxide is at least one selected from the group consisting of alumina and silicon oxide.

Optionally, a content of the forming agent in the acidic molecular sieve catalyst is m, and $0<m\leq 50$ wt %.

Specifically, an upper limit of the content of the forming agent in the acidic molecular sieve catalyst is selected from the group consisting of 10 wt %, 20 wt %, 40 wt %, and 50 wt %; and a lower limit of the content of the forming agent in the acidic molecular sieve catalyst is selected from the group consisting of 5 wt %, 10 wt %, 20 wt %, and 40 wt %.

Preferably, the content of the forming agent in the acidic molecular sieve catalyst is 15 wt % to 25 wt %.

Optionally, conditions of the reaction are as follows:

a reaction temperature is 60° C. to 260° C.;

a reaction pressure is 0.1 MPa to 10 MPa;

a molar ratio of the alkoxyacetate to the water is 1:20 to 20:1; and a weight hourly space velocity (WHSV) of the alkoxyacetate is 0.1 $h^{-1}$ to 3 $h^{-1}$.

Specifically, an upper limit of the reaction temperature is selected from the group consisting of 100° C., 150° C., and 260° C.; and a lower limit of the reaction temperature is selected from the group consisting of 60° C., 100° C., and 150° C.

An upper limit of the reaction pressure is selected from the group consisting of 0.3 MPa, 0.5 MPa, 1 MPa, 4 MPa, and 10 MPa; and a lower limit of the reaction pressure is selected from the group consisting of 0.1 MPa, 0.3 MPa, 0.5 MPa, 1 MPa, and 4 MPa.

An upper limit of the molar ratio of the alkoxyacetate to the water is selected from the group consisting of 1:10, 1:8, 1:4, 1:2, 1:1, 10:1, and 20:1; and a lower limit of the molar ratio of the alkoxyacetate to the water is selected from the group consisting of 1:20, 1:10, 1:8, 1:4, 1:2, 1:1, and 10:1.

An upper limit of the WHSV of the alkoxyacetate is selected from the group consisting of 0.3 $h^{-1}$, 1.0 $h^{-1}$, and 3.0 $h^{-1}$; and a lower limit of the WHSV of the alkoxyacetate is selected from the group consisting of 0.1 $h^{-1}$, 0.3 $h^{-1}$, and 1.0 $h^{-1}$.

Preferably, the conditions of the reaction are as follows:

a reaction temperature is 130° C. to 260° C.;

a reaction pressure is 0.1 MPa to 0.3 MPa;

a molar ratio of the alkoxyacetate to the water is 1:2 to 1:8; and a WHSV of the alkoxyacetate is 0.3 $h^{-1}$ to 1 $h^{-1}$.

Optionally, the reaction is conducted in at least one fixed-bed reactor; and when the reaction is conducted in a plurality of fixed-bed reactors, the plurality of fixed-bed reactors are connected in series and/or parallel.

Optionally, the reaction is conducted in an inactive atmosphere; and the inactive atmosphere includes any one selected from the group consisting of nitrogen and an inert gas.

Specifically, the inert gas may be argon.

In the present application, the term "alkyl group" refers to a group obtained after any hydrogen atom is removed from an alkane compound, where the alkane compound includes a cycloalkane, a linear alkane, and a branched alkane; and the "$C_1$-$C_5$" subscript indicates a number of carbon atoms in the group.

Possible beneficial effects of the present application:

1) The hydrolysis catalyst used in the present application is a molecular sieve catalyst with long life and high hydrolysis efficiency. The glycolic acid production method in the present application can be implemented by a traditional fixed-bed reactor under an atmospheric pressure, which is very suitable for continuous production. The raw material alkoxyacetate in the present application can be prepared by an environmentally-friendly and economical acetal carbonylation method.
2) When the raw material in the present application is methyl methoxyacetate, methanol and formaldehyde condensation to prepare DMM, DMM carbonylation to prepare methyl methoxyacetate, and methyl methoxyacetate hydrolysis to prepare glycolic acid can be used in combination to allow efficient, environmentally-friendly, and economical conversion of methanol (a platform chemical in the coal chemical industry) into glycolic acid.

DETAILED DESCRIPTION OF THE EMBODIMENTS

The present application will be described in detail below with reference to embodiments, but the present application is not limited to these embodiments.

Unless otherwise specified, the raw materials in the embodiments of the present application all are purchased from commercial sources.

Possible embodiments are described below.

Specifically, the present application provides a method for preparing glycolic acid through hydrolysis of alkoxyacetate, where raw materials of alkoxyacetate and water are allowed to pass through a reaction zone loaded with an acidic molecular sieve catalyst, such that the raw materials undergo a reaction under specified conditions to produce glycolic acid.

The alkoxyacetate has a structural formula as follows:

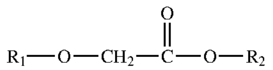

where $R_1$ is any one selected from the group consisting of methyl ($CH_3$), ethyl ($C_2H_5$), propyl ($C_3H_7$), and butyl ($C_4H_9$); $R_2$ is any one selected from the group consisting of methyl ($CH_3$), ethyl ($C_2H_5$), propyl ($C_3H_7$), and butyl ($C_4H_9$); and $R_1$ and $R_2$ can be the same or different.

The acidic molecular sieve is a molecular sieve with acidity.

The reaction zone includes a single fixed-bed reactor, or a plurality of fixed-bed reactors connected in series and/or parallel.

Conditions of the reaction are as follows: a reaction temperature is 60° C. to 260° C., a molar ratio of the alkoxyacetate to the water is 1:20 to 20:1, a reaction pressure is 0.1 MPa to 10 MPa, and a WHSV of the alkoxyacetate is 0.1 $h^{-1}$ to 3 $h^{-1}$.

A reaction equation for hydrolysis of the alkoxyacetate is as follows:

$$R_1OCH_2COOR_2 + 2\,H_2O = R_1OH + R_2OH + HOCH_2COOH. \quad (1)$$

There are also two partial hydrolysis reactions for the alkoxyacetate as follows:

$$R_1OCH_2COOR_2 + H_2O = R_2OH + R_1OCH_2COOH \text{ and} \quad (2)$$

$$R_1OCH_2COOR_2 + H_2O = R_1OH + HOCH_2COOR_2. \quad (3)$$

Products of the two partial hydrolysis reactions can be further hydrolyzed under the same catalyst and reaction conditions to produce glycolic acid:

$$R_1OCH_2COOH + H_2O = R_1OH + HOCH_2COOH \text{ and} \quad (4)$$

$$HOCH_2COOR_2 + H_2O = R_2OH + HOCH_2COOH. \quad (5)$$

In addition, alcohols $R_1OH$ and $R_2OH$ resulting from hydrolysis can also be partially dehydrated to produce corresponding ethers.

The acidic molecular sieve is one or a mixture of two or more selected from the group consisting of an acidic MFI-structured molecular sieve, an acidic FAU-structured molecular sieve, an acidic FER-structured molecular sieve, an acidic BEA-structured molecular sieve, an acidic MOR-structured molecular sieve, and an acidic MWW-structured molecular sieve.

The acidic molecular sieve is one or a mixture of two or more selected from the group consisting of an acidic ZSM-5 molecular sieve, an acidic Y molecular sieve, an acidic ZSM-35 molecular sieve, an acidic β molecular sieve, an acidic MOR molecular sieve, and an acidic MCM-22 molecular sieve.

The acidic molecular sieve is one or a mixture of two or more selected from the group consisting of a hydrogen-type ZSM-5 molecular sieve, a hydrogen-type Y molecular sieve, a hydrogen-type ZSM-35 molecular sieve, a hydrogen-type β molecular sieve, a hydrogen-type MOR molecular sieve, and a hydrogen-type MCM-22 molecular sieve.

A Si/Al atom ratio of the acidic molecular sieve is 3 to 500.

In addition to an acidic molecular sieve, the acidic molecular sieve catalyst further includes a catalyst forming agent; and the catalyst forming agent is one selected from the group consisting of alumina and silicon oxide, and has a weight percentage content of 0% to 50%.

The acidic molecular sieve catalyst is prepared by mixing the catalyst forming agent and the acidic molecular sieve and molding a resulting mixture into a strip.

In the alkoxyacetate, $R_1$ and $R_2$ both are methyl, that is, the alkoxyacetate is methyl methoxyacetate ($CH_3OCH_2COOCH_3$).

The methyl methoxyacetate is prepared by a DMM carbonylation method.

When the alkoxyacetate is methyl methoxyacetate, according to principles of reactions (1) to (5), hydrolysis products include glycolic acid, methoxyacetic acid ($CH_3OCH_2COOH$), methyl glycolate ($HOCH_2COOCH_3$), methanol, and dimethyl ether (DME). The methoxyacetic acid and methyl glycolate can be further hydrolyzed into glycolic acid, and methanol and DME can be returned to a DMM synthesis reactor to synthesize DMM.

When the alkoxyacetate is methyl methoxyacetate, according to the principles of reactions (1) to (5), the selectivity of the hydrolysis product glycolic acid can be as high as 50% based on a carbon number calculation theory.

The conditions of the reaction are preferably as follows: a reaction temperature is 130° C. to 200° C., a molar ratio of the alkoxyacetate to the water is 1:8 to 1:2, a reaction pressure is 0.1 MPa to 0.3 MPa, and a WHSV of the alkoxyacetate is 0.3 $h^{-1}$ to 1 $h^{-1}$.

When the raw materials are allowed to pass through a reaction zone loaded with an acidic molecular sieve catalyst, an inert carrier gas selected from the group consisting of nitrogen and argon is introduced.

Analysis methods and conversion rate and selectivity calculation in the embodiments are as follows:

An Agilent7890B gas chromatograph is used to analyze products other than glycolic acid and unreacted raw materials, where an FID detector is connected to a DB-FFAP capillary column and a TCD detector is connected to a Porapak Q packed column. A liquid chromatograph is used to analyze glycolic acid, where a separation column is a Cis column and a detector is an ultraviolet (UV) detector.

In an embodiment of the present application, both a conversion rate and selectivity are calculated based on a mole number of carbon:

alkoxyacetate conversion rate=[(mole number of carbon in fed alkoxyacetate)−(mole number of carbon in discharged alkoxyacetate)]÷(mole number of carbon in fed alkoxyacetate)×100% and selectivity for a product=(mole number of carbon in a discharged product)÷(total mole number of carbon in all discharged carbon-containing products)×100%.

The present application will be described in detail below with reference to examples, but the present application is not limited to these examples.

Catalyst Performance Test

Example 1

An acidic H-ZSM-5 molecular sieve with a Si/Al ratio of 20 produced by Zhongke Catalysis New Technology (Dalian) Co., Ltd. was selected, crushed, and sieved to obtain 0.4 mm to 0.8 mm particles; 2 g of the particles was taken and filled into a stainless steel reaction tube with an inner diameter of 8 mm and activated with 50 mL/min nitrogen at 500° C. for 4 h; a reaction was conducted for 24 h under the following conditions: a reaction temperature (T) was 150° C., and a reaction pressure (P) was 0.1 MPa; a molar ratio of methyl methoxyacetate to water was 1:4; and a WHSV of methyl methoxyacetate was 1.0 $h^{-1}$; and after the reaction was completed, products were analyzed by gas chromatography and liquid chromatography. Reaction results based on a mole number of carbon were shown in Table 1.

Examples 2 to 9

The catalyst, reaction conditions, and reaction results were shown in Table 1. Other operations were the same as in Example 1.

TABLE 1

Catalytic reaction results in Examples 1 to 9

| Example | Acidic molecular sieve catalyst | Manufacturer | Si/Al ratio | Reaction conditions | Methyl methoxy acetate conversion rate (%) | Glycolic acid selectivity (%) | Methyl glycolate selectivity (%) | Methoxyacetic acid selectivity (%) | Methanol and DME selectivity (%) |
|---|---|---|---|---|---|---|---|---|---|
| 1 | H-ZSM-5 | Zhongke Catalysis New Technology (Dalian) Co., Ltd. | 20 | T = 150° C., P = 0.1 MPa, WHSV = 1.0 $h^{-1}$, and methyl methoxyacetate:water = 1:4 | 81.2 | 36.4 | 7.3 | 8.1 | 48.2 |
| 2 | H-Y | Zhongke Catalysis New Technology (Dalian) Co., Ltd. | 3 | T = 150° C., P = 0.1 MPa, WHSV = 1.0 $h^{-1}$, and methyl methoxyacetate:water = 1:4 | 60.3 | 30.4 | 14.4 | 10.0 | 45.2 |
| 3 | H-ZSM-35 | Catalyst Plant of Nankai University | 50 | T = 150° C., P = 0.1 MPa, WHSV = 1.0 $h^{-1}$, and methyl methoxyacetate:water = 1:4 | 78.9 | 37.0 | 7.5 | 7.0 | 48.5 |
| 4 | H-β | Zhongke Catalysis New Technology (Dalian) Co., Ltd. | 500 | T = 150° C., P = 0.1 MPa, WHSV = 1.0 $h^{-1}$, and methyl methoxyacetate:water = 1:4 | 40.3 | 26.2 | 10.7 | 20.0 | 43.1 |
| 5 | H-Mordenite | Yanchang Zhongke (Dalian) Energy Technology Co., Ltd. | 10 | T = 150° C., P = 0.1 MPa, WHSV = 1.0 $h^{-1}$, and methyl methoxyacetate:water = 1:4 | 50.7 | 29.0 | 14.0 | 12.5 | 44.5 |
| 6 | H-MCM-22 | Yanchang Zhongke (Dalian) Energy Technology Co., Ltd. | 100 | T = 150° C., P = 0.1 MPa, WHSV = 1.0 $h^{-1}$, and methyl methoxyacetate:water = 1:4 | 37.9 | 34.2 | 7.7 | 11.0 | 47.1 |
| 7 | H-ZSM-5 | Zhongke Catalysis New Technology (Dalian) Co., Ltd. | 20 | T = 260° C., P = 10 MPa, WHSV = 3.0 $h^{-1}$, and methyl methoxyacetate:water = 1:20 | 88.6 | 32.4 | 14.3 | 7.1 | 46.2 |
| 8 | H-ZSM-5 | Zhongke Catalysis New Technology (Dalian) Co., Ltd. | 20 | T = 60° C., P = 0.3 MPa, WHSV = 0.1 $h^{-1}$, and methyl methoxyacetate:water = 20:1 | 2.0 | 11.0 | 28.5 | 30.0 | 30.5 |

TABLE 1-continued

Catalytic reaction results in Examples 1 to 9

| Example | Acidic molecular sieve catalyst | Manufacturer | Si/Al ratio | Reaction conditions | Methyl methoxy acetate conversion rate (%) | Glycolic acid selectivity (%) | Methyl glycolate selectivity (%) | Methoxyacetic acid selectivity (%) | Methanol and DME selectivity (%) |
|---|---|---|---|---|---|---|---|---|---|
| 9 | H-ZSM-5 | Zhongke Catalysis New Technology (Dalian) Co., Ltd. | 20 | T = 150° C., P = 0.1 MPa, WHSV = 1.0 $h^{-1}$, methyl methoxyacetate:water = 1:4, and nitrogen = 50 mL/min | 77.6 | 36.0 | 8.9 | 7.1 | 48.0 |

It can be seen from Table 1 that the hydrogen-type molecular sieve catalyst leads to a high methyl methoxyacetate conversion rate and high glycolic acid selectivity during the hydrolysis of methyl methoxyacetate to produce glycolic acid, indicating excellent catalytic performance.

Examples 10 to 13

Another alkoxyacetate was used instead of the methyl methoxyacetate in Example 1, and other conditions and operations remained unchanged. Reaction results were shown in Table 2.

TABLE 2

Catalytic reaction results in Examples 1 and 10 to 13

| Example | Alkoxyacetate | Alkoxyacetate conversion rate (%) | Glycolic acid selectivity (%) |
|---|---|---|---|
| 1 | Methyl methoxyacetate $CH_3OCH_2COOCH_3$ | 81.2 | 36.4 |
| 10 | Ethyl methoxyacetate $CH_3OCH_2COOC_2H_5$ | 80.5 | 28.1 |
| 11 | n-Propyl methoxyacetate $CH_3OCH_2COOC_3H_7$ | 83.9 | 25.1 |
| 12 | n-Butyl methoxyacetate $CH_3OCH_2COOC_4H_9$ | 78.8 | 25.3 |
| 13 | Ethyl ethoxyacetate $C_2H_5OCH_2COOC_2H_5$ | 79.1 | 31.1 |

It can be seen from Table 2 that the hydrogen-type molecular sieve catalyst can hydrolyze various types of Malkoxyacetate into glycolic acid.

Examples 14 to 15

The acidic H-ZSM-5 molecular sieve with a Si/Al ratio of 20 in Example 1 was molded with alumina or silicon oxide into a strip, and after the molding, a content of the alumina or silicon oxide in the molded catalyst was 20 wt %. Other conditions and operations remained unchanged. Reaction results were shown in Table 3.

TABLE 3

Catalytic reaction results in Examples 1, 14, and 15

| Example | Forming agent | Methyl methoxyacetate conversion rate (%) | Glycolic acid selectivity (%) |
|---|---|---|---|
| 1 | None | 81.2 | 36.4 |
| 14 | Alumina | 77.5 | 35.3 |
| 15 | Silicon oxide | 76.8 | 35.0 |

It can be seen from Table 3 that the catalytic activity of the acidic molecular sieve catalyst remains basically unchanged after the molding with alumina or silicon oxide.

Example 16

An acidic H-ZSM-5 molecular sieve with a Si/Al ratio of 20 produced by Zhongke Catalysis New Technology (Dalian) Co., Ltd. was selected, crushed, and sieved to obtain 0.4 mm to 0.8 mm particles; 2 g of the particles was taken and filled into a stainless steel reaction tube with an inner diameter of 8 mm and activated with 50 mL/min nitrogen at 500° C. for 4 h; a reaction was conducted under the following conditions: a reaction temperature (T) was 150° C., and a reaction pressure (P) was 0.1 MPa; a molar ratio of methyl methoxyacetate to water was 1:4; and a WHSV of methyl methoxyacetate was 1.0 $h^{-1}$; and products at different time points were analyzed by gas chromatography and liquid chromatography. Reaction results based on a mole number of carbon were shown in Table 4.

TABLE 4

Catalytic reaction results in Example 16

| Reaction time (h) | Methyl methoxyacetate conversion rate (%) | Glycolic acid selectivity (%) |
|---|---|---|
| 24 | 81.2 | 36.4 |
| 100 | 81.1 | 36.3 |
| 500 | 81.0 | 36.5 |
| 1000 | 80.6 | 36.1 |
| 2000 | 79.9 | 35.7 |
| 4000 | 76.6 | 35.2 |
| 8000 | 73.2 | 34.8 |

It can be seen from Table 4 that the acidic molecular sieve catalyst exhibits excellent stability in the hydrolysis of methyl methoxyacetate to produce glycolic acid, and can meet the requirements of industrial use.

The above examples are merely few examples of the present application, and do not limit the present application in any form. Although the present application is disclosed as above with preferred examples, the present application is not limited thereto. Some changes or modifications made by any technical personnel familiar with the profession using the technical content disclosed above without departing from the scope of the technical solutions of the present application are equivalent to equivalent implementation cases and fall within the scope of the technical solutions.

What is claimed is:

1. A method for preparing glycolic acid through a hydrolysis of alkoxyacetate, comprising: subjecting raw materials comprising the alkoxyacetate and water to a reaction in the presence of an acidic molecular sieve catalyst to produce the glycolic acid, wherein the alkoxyacetate is at least one selected from the group consisting of compounds with a structural formula shown in formula I:

formula I

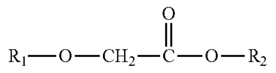

wherein $R_1$ and $R_2$ each are independently one selected from the group consisting of $C_1$-$C_5$ alkyl groups.

2. The method according to claim 1, wherein $R_1$ is one selected from the group consisting of methyl, ethyl, propyl, and butyl; and $R_2$ is one selected from the group consisting of methyl, ethyl, propyl, and butyl.

3. The method according to claim 1, wherein the acidic molecular sieve catalyst is at least one selected from the group consisting of an acidic MFI-structured molecular sieve, an acidic FAU-structured molecular sieve, an acidic FER-structured molecular sieve, an acidic BEA-structured molecular sieve, an acidic mordenite (MOR)-structured molecular sieve, and an acidic MWW-structured molecular sieve.

4. The method according to claim 3, wherein the acidic molecular sieve catalyst is at least one selected from the group consisting of an acidic ZSM-5 molecular sieve, an acidic Y molecular sieve, an acidic ZSM-35 molecular sieve, an acidic β molecular sieve, an acidic MOR molecular sieve, and an acidic MCM-22 molecular sieve.

5. The method according to claim 4, wherein the acidic molecular sieve catalyst is at least one selected from the group consisting of a hydrogen-type ZSM-5 molecular sieve, a hydrogen-type Y molecular sieve, a hydrogen-type ZSM-35 molecular sieve, a hydrogen-type β molecular sieve, a hydrogen-type MOR molecular sieve, and a hydrogen-type MCM-22 molecular sieve.

6. The method according to claim 1, wherein a Si/Al atom ratio of the acidic molecular sieve catalyst is 3 to 500.

7. The method according to claim 1, wherein the acidic molecular sieve catalyst further comprises a forming agent;

the forming agent is an oxide;

the oxide is at least one selected from the group consisting of alumina and silicon oxide; and a content of the forming agent in the acidic molecular sieve catalyst is m, and $0<m\leq 50$ wt %.

8. The method according to claim 1, wherein conditions of the reaction are as follows:

a reaction temperature is 60° C. to 260° C.;

a reaction pressure is 0.1 MPa to 10 MPa;

a molar ratio of the alkoxyacetate to the water is 1:20 to 20:1; and a weight hourly space velocity (WHSV) of the alkoxyacetate is 0.1 $h^{-1}$ to 3 $h^{-1}$.

9. The method according to claim 8, wherein the conditions of the reaction are as follows:

the reaction temperature is 130° C. to 260° C.;

the reaction pressure is 0.1 MPa to 0.3 MPa;

the molar ratio of the alkoxyacetate to the water is 1:2 to 1:8; and the WHSV of the alkoxyacetate is 0.3 $h^{-1}$ to 1 $h^{-1}$.

10. The method according to claim 1, wherein the reaction is conducted in one fixed-bed reactor or a plurality of fixed-bed reactors.

11. The method according to claim 10, wherein the plurality of fixed-bed reactors are connected in series and/or parallel.

12. The method according to claim 1, wherein the reaction is conducted in an inactive atmosphere; and the inactive atmosphere comprises one selected from the group consisting of nitrogen and an inert gas.

* * * * *